(12) United States Patent
Ocio et al.

(10) Patent No.: US 8,435,992 B2
(45) Date of Patent: *May 7, 2013

(54) MULTIPLE MYELOMA TREATMENTS

(75) Inventors: Enrique Ocio, Salamanca (ES);
Atanasio Pandiella, Salamanca (ES);
Jesús San Miguel, Salamanca (ES);
Pablo Manuel Avilés Marín, Madrid (ES)

(73) Assignee: Pharma Mar S.A., Madrid (ES)

( * ) Notice: Subject to any disclaimer, the term of this patent is extended or adjusted under 35 U.S.C. 154(b) by 89 days.

This patent is subject to a terminal disclaimer.

(21) Appl. No.: 12/992,754

(22) PCT Filed: May 18, 2009

(86) PCT No.: PCT/EP2009/055978
§ 371 (c)(1),
(2), (4) Date: Nov. 15, 2010

(87) PCT Pub. No.: WO2009/138509
PCT Pub. Date: Nov. 19, 2009

(65) Prior Publication Data
US 2011/0076343 A1  Mar. 31, 2011

(30) Foreign Application Priority Data

May 16, 2008 (EP) ..................................... 08380154

(51) Int. Cl.
*A61K 31/4995* (2006.01)
*A61P 35/00* (2006.01)
*C07C 35/44* (2006.01)

(52) U.S. Cl.
USPC ................. 514/250; 514/252.12; 514/255.03; 544/338; 544/384; 544/400

(58) Field of Classification Search .......................... None
See application file for complete search history.

(56) References Cited

U.S. PATENT DOCUMENTS

| | | |
|---|---|---|
| 6,348,467 B1 | 2/2002 | Corey |
| 6,569,859 B1 | 5/2003 | Corey |
| 7,247,629 B2 | 7/2007 | Manzanares et al. |
| 7,410,969 B2 | 8/2008 | Manzanares et al. |
| 7,723,068 B2 | 5/2010 | Iglesias et al. |
| RE41,614 E | 8/2010 | Corey |
| 2006/0172926 A1* | 8/2006 | Bertino et al. ................ 514/10 |

FOREIGN PATENT DOCUMENTS

| | | |
|---|---|---|
| WO | WO 01/87894 | * 11/2001 |
| WO | WO 2008/135792 | 11/2008 |

OTHER PUBLICATIONS

Kuehl et al. Nature Reviews/Cancer 2002, 2, 175-187.*
Richardson et al. Blood 2006, 108 (10), 3458-3464.*
Rajkumar et al. Blood 2005, 106 (13), 4050-4053.*
Elices et al. Antitumor activity of the novel investigational compound PM00104 [Abstract]. In Proceedings of the 96th Annual Meeting of the American Association for Cancer Research 2005, Apr. 16-20, Anaheim, CA; AACR Meeting Abstracts 2005, p. 1385, Abstract No. 5882.*
U.S. Appl. No. 11/645,356, filed Dec. 22, 2006, Ignacio Manzanares.
U.S. Appl. No. 12/091,540, filed Jun. 4, 2008, Pilar Calvo Salve.
U.S. Appl. No. 12/337,756, filed Dec. 18, 2008, Elias J Corey.
U.S. Appl. No. 12/992,812, filed Nov. 15, 2010, Doreen LePage.
Capdevila, J. et al., "Phase I study of the novel anticancer drug PM00104 as a 24-hour IV infusion every 3 weeks (q3w) in patients (pts) with advanced solid tumors or lymphoma," Journal of Clinical Oncology, 2009 ASCO Annual Meeting Proceedings: vol. 27, No. 15S (May 20 Supplement), 2009:2568; and the corresponding poster presented in said congress.
Colado, E. et al., "Zalypsis possess potent antileukemic effect through the induction of a DNA damage response, independently of the p53 status," ASH Annual Meeting Abstracts, 2009 114:Abstract 3792; and the corresponding poster presented in said congress.
Colado, E. et al., "Zalypsis, a novel and selective antileukemic agent targeting immature blast cell populations," In: 13th congress of the European Hematology Association, Jun. 4-7, 2009, Berlin, Germany. Abstract No. 3792; and the corresponding poster presented in said congress.
Dimopoulos, M. et al., "Lenalidomide plus Dexamethasone for Relapsed or Refractory Multiple Myeloma," N. Engl. J. Med., 2007, 357, 2123-2132.
Fontana, A. et al., "A New Antitumor Isoquinoline Alkaloid from the Marine Nudibranch *Jorunna funebris*," Tetrahedron, 2000, 56, 7305-7308.
Frapolli, R. et al., "The pattern of in vivo biological activity of Zalypsis® is different from that of trabectedin," In: 21st AACR-NCI-EORTC International Conference on Molecular Targets and Cancer Therapeutics; Nov. 15-26, 2009; Boston, MA. Philadelphia (PA): AACR, 2009. Abstract No. B198; and the corresponding poster presented in said congress.
Frincke et al., "Antimicrobial Metabolites of the Sponge *Reniera* sp.," J. Am. Chem. Soc., 1982, 104, 265-269.

(Continued)

*Primary Examiner* — Sreeni Padmanabhan
*Assistant Examiner* — Irina Neagu
(74) *Attorney, Agent, or Firm* — Kenneth H. Sonnenfeld; King & Spalding (57) ABSTRACT

Methods for treating cancer by using compound PM00104, in particular, for treating multiple myeloma are provided.

7 Claims, 8 Drawing Sheets

OTHER PUBLICATIONS

Gallerani, E. et al., "Phase I study of PM00104, a novel cytotoxic anticancer drug, administered to patients with advanced solid tumors or lymphoma," *Journal of Clinical Oncology*, 2007 ASCO Annual Meeting Proceedings Part I. vol. 25, No. 18S (Jun. 20 Supplement), 2007:2517; and the corresponding poster presented in said congress.

Guillén, M. J. et al., "Antitumor activity of PM00104 in hepatocellular carcinoma (HCC) experimental models," In: Proceedings of the 100th Annual Meeting of American Associates for Cancer Research; Apr. 18-22, 2009; Denver, CO. Philadelphia (PA): AACR, 2009. Abstract No. 2018; and the corresponding oral presentation presented in said congress.

Guillén, M. J. et al., "Evaluation of antitumor activity of PM00104 combined with Cisplatin in experimental models of bladder and gastric tumors," In: Proceedings of the 100th Annual Meeting of American Associates for Cancer Research; Apr. 18-22, 2009; Denver, CO. Philadelphia (PA): AACR, 2009. Abstract No. 2682; and the corresponding poster presented in said congress.

Guirouilh-Barbat, J. et al., "Zalypsis (PM00104) is a potent inducer of γ-H2AX foci and reveals the importance of the C ring of trabectedin for transcription-coupled repair inhibition," Mol. Cancer Ther., 2009, 8, 2007-2014.

Leal, J. F. M. et al., "Molecular pharmacology and antitumor activity of Zalypsis® in several human cancer cell lines," Biochem. Pharmcol. 2009, 78, 162-170.

Manzanares, I. et al., "Advances in the Chemistry and Pharmacology of Ecteinascidins, A Promising New Class of Anticancer Agents," Curr. Med. Chem.—Anti-cancer Agents, 2001, 1, 257-276.

Martínez-Leal, J. F. et al., "P53 status correlatos with the sensitivity to PM00104 in human cancer cell lines," In: Proceedings of the 100th Annual Meeting of American Associates for Cancer Research; Apr. 18-22, 2009; Denver, CO. Philadelphia (PA): AACR, 2009. Abstract No. 4527; and the corresponding poster presented in said congress.

Ocio, E. M. et al., "DNA Double Strands Breaks Induction by Zalypsis, a Novel Marine Compound, Results in Potent Antimyeloma Activity," Blood (ASH Annual Meeting Abstracts) 2008 112: Abstract No. 245; and the corresponding oral presentation presented in said congress.

Ocio, E.M. et al., "Zalypsis: A novel marine-derived compound with potent antimyeloma activity that reveals high sensitivity of malignant plasma cells to DNA double-strand breaks," Blood, 2009, 113, 3781-3791.

Ocio, E. M. et al., "Zalypsis (PM00104): A very potent in vitro and in vivo inductor of apoptosis in myeloma cells based on a p53-dependent response," In: 13th congress of the European Hematology Association, Jun. 12-15, 2008, Copenhagen, Denmark. Abstract No. 0789; and the corresponding poster presented in said congress.

Plummer, R. et al., "Phase I, open-label, dose-escalating clinical and pharmacokinetic study of PM00104 administered weekly resting every fourth week, intravenously, over 1 hour to patients with advanced malignant solid tumors or lymphoma," In: 21st AACR-NCI-EORTC International Conference on Molecular Targets and Cancer Therapeutics; Nov. 15-26, 2009, Boston, MA. Philadelphia (PA): AACR, 2009. Abstract No. B149; and the corresponding poster presented in said congress.

Richardson, P. G. et al., "Bortezomib or High-Dose Dexamethasone for Relapsed Multiple Myeloma," N. Engl. J. Med., 2005, 352, 2487-2498.

Richardson, P. G. et al., "Immunodulatory drug CC-5013 overcomes drug resistance and is well tolerated in patients with relapsed multiple myeloma," Blood, 2002, 100, 3063-3067.

Soria, J. C. et al., "Phase I study of the novel anti-cancer drug PM00104 as a 1-hour weekly infusion resting every fourth week in patients with advanced solid tumors or lymphoma, "In: 20th AACR-NCI-EORTC International Conference on Molecular Targets and Cancer Therapeutics; Oct. 22-24, 2008; Geneva, Switzerland. Philadelphia (PA): AACR, 2008. Abstract No. 179; and the corresponding poster presented in said congress.

Weber, D. M. et al., "Lenalidomide plus Dexamethasone for Relapsed Multiple Myeloma in North America," N. Engl. J. Med., 2007, 357, 2133-2142.

* cited by examiner

MULTIPLE MYELOMA TREATMENTS

The present invention relates to the treatment of cancers and, in particular, to the effective treatment of multiple myeloma by using compound PM00104.

BACKGROUND OF THE INVENTION

Multiple myeloma represents a malignant proliferation of plasma cells derived from a single clone. The terms multiple myeloma and myeloma are used interchangeably.

Plasma cells produce antibodies, proteins that move through the bloodstream to help the body get rid of harmful substances. Each type of plasma cell responds to only one specific substance by making a large amount of one kind of antibody. These antibodies find and act against that one substance. Because the body has many types of plasma cells, it can respond to many substances. When cancer involves plasma cells, the body keeps producing more and more of these cells. The unneeded plasma cells—all abnormal and all exactly alike—are called myeloma cells. Myeloma cells tend to collect in the bone marrow and in the hard outer part of bones. Sometimes they collect in only one bone and form a single mass, or tumor, called a plasmacytoma. In most cases, however, the myeloma cells collect in many bones, often forming many tumors and causing other problems. When this happens, the disease is called multiple myeloma (MM).

Because people with MM have an abnormally large number of identical plasma cells, they also have too much of one type of antibody. The tumor, its products, and the host response to it result in a number of organ dysfunctions and symptoms of bone pain or fracture, renal failure, susceptibility to infection, anemia, hypercalcemia, and occasionally clotting abnormalities, neurologic symptoms, and vascular manifestations of hyperviscosity.

MM is the $2^{nd}$ most commonly diagnosed hematologic malignancy in the Western World, with an annual incidence of ~15,000 new cases in the U.S. alone, and is the $14^{th}$ cause of death by cancer when considering all tumors. Unfortunately, MM is presently considered an incurable disease and the overall survival of MM patients has remained essentially unchanged at a median of 3-4 years, despite intense efforts over the last ~3 decades to improve on the activity of cytotoxic chemotherapy-based therapies for this disease. Importantly, the median age of diagnosis of MM is <65 years old and >⅓ of MM patients are <55 years old at diagnosis. For this substantial proportion of relatively young MM patients, the diagnosis of MM signifies, even in the absence of other co-morbidities, a high probability that their overall survival will be significantly shorter than the average life-expectancy of age-matched non-MM patients.

Recently, there have been a series of important advances in the therapeutic management of MM, namely the documentation of anti-MM activity of two new classes of anti-cancer agents: thalidomide (and its immunomodulatory derivatives such as lenalidomide (Dimopoulos M et al. N. Engl. J. Med. 2007, 357, 2123-2132; Weber D M et al. N. Engl. J. Med. 2007, 357, 2133-2142)) and the proteasome inhibitors such as bortezomib (Richardson P G et al. N. Engl. J. Med. 2005, 352, 2487-2498). Although these classes of agents have been shown to be active in the setting of MM patients who were relapsed/refractory to conventional or high-dose cytotoxic chemotherapy-based regimens, a significant proportion of MM patients has de novo resistance to those novel agents, while initial responders (even those achieving durable complete remissions) can eventually relapse. Therefore the development of novel classes of anti-MM agents is urgently needed, in order to further improve the outcome of MM patients and, hopefully, to achieve high cure rates for this presently incurable neoplasia.

More information about MM can be found in the medical literature such as in the "Handbook Cancer. Principles & Practice of Oncology", 7th ed. Philadelphia, Pa.: Lippincott Williams & Wilkins, 2005.

PM00104 is an alkaloid related to Jorumycin and Renieramycins, and also to safracin and saframycin compounds. Jorumycin is a natural compound isolated from the skin and from the mucus of the Pacific nudibranch *Jorunna funebris* (Fontana A., et al., Tetrahedron (2000), 56, 7305-8). In addition, the family of Renieramycins is disclosed as being isolated from sponges and tunicates (James M. F. et al. J. Am. Chem. Soc. (1982), 104, 265-269; Oku N., et al. Journal Natural Products (2003), 66, 1136-9). Safracin and saframycin compounds are disclosed in Manzanares I., et al. Curr. Med. Chem. Anti-Cancer Agents (2001), 1, 257-276, as well as in WO 00/18233 and WO 01/87894.

PM00104 has demonstrated a significant in vitro activity against solid and non-solid tumour cell lines as well as significant in vivo activity in several xenografted human cell lines in mice, such as breast and prostate cancer lines. Preliminary insights into the mechanism of action of PM00104 suggested cell cycle changes, DNA binding properties and transcriptional inhibition. For further details of PM00104 see WO 01/87894. This compound shows the following chemical structure:

Additionally, the reader is referred to WO 2007/052076 and WO 2008/135792, which are incorporated herein by specific reference, for pharmaceutical compositions and administration dosages and schedules of PM00104.

It is an object of the present invention to provide new and improved forms of treatment of MM by using PM00104.

It is another object of the present invention to provide new uses in cancer therapy for PM00104.

SUMMARY OF THE INVENTION

We have established for the first time that PM00104 has antitumor activity against multiple myeloma (MM), and therefore that it can be successfully used in the treatment of this disease.

Thus, this invention is directed to pharmaceutical compositions, kits, methods for the treatment of MM using PM00104, and uses of PM00104 in the manufacture of a medicament for the treatment of MM.

In accordance with one aspect of this invention, we provide for the treatment of a patient in need thereof with a therapeutically effective amount of PM00104, or a pharmaceutical acceptable salt thereof, for the treatment of MM.

In a related embodiment, the invention further provides for the use of PM00104, or a pharmaceutically acceptable salt thereof, in the preparation of a medicament for the treatment of MM.

In a further aspect, the invention provides PM00104, or a pharmaceutically acceptable salt thereof, for use in the treatment of MM.

In another aspect, the present invention is also directed to a pharmaceutical composition comprising PM00104, or a pharmaceutical acceptable salt thereof, and a pharmaceutically acceptable carrier or excipient, to be used in the treatment of MM.

The present invention additionally provides a method for treating any mammal, notably a human, affected by MM, comprising administering to the affected individual a therapeutically effective amount of PM00104, or a pharmaceutical acceptable salt thereof.

In a further aspect of the present invention, a medical kit for administering PM00104 is provided, comprising printed instructions for administering PM00104 according to the uses and methods of treatment set forth herein, and a pharmaceutical composition comprising PM00104, or a pharmaceutical acceptable salt thereof, and a pharmaceutically acceptable carrier or excipient.

BRIEF DESCRIPTION OF THE FIGURES

FIG. 1. PM00104 inhibits the viability of multiple myeloma cells while preserving normal hematopoietic progenitor cells. Nine MM cell lines were incubated with different concentrations of PM00104 for 24 (FIG. 1A), 48 (FIG. 1B) and 72 hours (FIG. 1C) and cell viability was analyzed by MTT assay. The average proliferation values of control untreated samples were taken as 100%. Data is represented as the mean±SD of quadruplicates of an experiment that was repeated at least twice.

FIG. 3. PM00104 overcomes the protective effects of IL-6, IGF-I, and adherence to patient BMSCs. MM1S cells were treated for 48 hours with indicated concentrations of PM00104 in the presence or absence of IL-6 (FIG. 3A), IGF-I (FIG. 3B), or BMSCs derived from a MM patient (FIG. 3C). DNA synthesis was determined by measuring BrdU incorporation during the last 8 hours of 48-hour cultures. Additionally, BMSCs were cultured with different doses of PM00104 for 48 hours and the cytotoxicity was analyzed by MTT assay (FIG. 3D). Data is presented as the mean±SD of quadruplicates.

FIG. 4. In vivo antimyeloma effect. Evolution of the volume of MM1S (FIG. 4A) and OPM-1 plasmocytomas (FIG. 4C) for the indicated days, and survival of treated MM1S (FIG. 4B) and OPM-1 (FIG. 4D) mice.

FIG. 5. PM00104 potentiates the antimyeloma action of conventional and novel antimyeloma agents. MM1S cells were treated with suboptimal concentrations of PM00104 (Zalypsis, Z) and other antimyeloma agents such as Dexamethasone (Dex), melphalan (Mel), doxorubicin (Dox), bortezomib (Bort) and lenalidomide (Len) in double (FIG. 5A) and triple combinations (FIG. 5B). Cell viability was analyzed by MTT assay.

DETAILED DESCRIPTION OF THE INVENTION

Despite recent advances in the therapeutic management of MM, there is still the need to identify novel therapeutic agents with anti-MM activity, especially in patients who relapse or do not optimally respond to conventionally and/or novel therapies.

We found that PM00104 presents strong anti-MM activity, both in in vitro and in vivo assays. In the in vitro studies, PM00104 potently acted on MM cell lines as well as on patient cells, and its $IC_{50}$ values for most of the cell lines were in the low nanomolar or picomolar range, indicating superiority over all other drugs used in the MM therapy. Furthermore, PM00104 synergized with several of these current MM treatments, supporting the possibility of using this drug in combination with those other well established drugs. Interestingly, PM00104 was also equally efficient on cell lines, such as MM1R and RPMI-LR5, selected for their resistance to conventional anti-MM treatments, indicating that this drug could be used to overcome drug resistance, a common situation found in treated MM patients. In addition to the in vitro results, in vivo animal studies confirmed the anti-MM activity of PM00104. The drug appeared to be well tolerated, and profoundly affected the growth of xenografted plasmacytomas of MM1S and OPM-1 in mice.

The term "treating", as used herein, unless otherwise indicated, means reversing, alleviating, inhibiting the progress of, attenuating the symptoms or pathological basis of the disease, or preventing the disorder or condition to which such term applies, or one or more symptoms of such disorder or condition. The term "treatment", as used herein, unless otherwise indicated, refers to the act of treating as "treating" is defined immediately above.

As mentioned above, PM00104 is an alkaloid related to the marine compounds Jorumycin and Renieramycins, and also to safracin and saframycin compounds, having the following structure:

The term "PM00104" is intended here to cover any pharmaceutically acceptable salt, solvate, hydrate, prodrug, or any other compound which, upon administration to the patient is capable of providing (directly or indirectly) the compound as described herein. The preparation of salts, solvates, hydrates, and prodrugs can be carried out by methods known in the art.

Pharmaceutically acceptable salts can be synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

Any compound that is a prodrug of PM00104 is within the scope and spirit of the invention. The term "prodrug" is used in its broadest sense and encompasses those derivatives that are converted in vivo to PM00104. The prodrug can hydrolyze, oxidize, or otherwise react under biological conditions to provide PM00104. Examples of prodrugs include, but are not limited to, derivatives and metabolites of PM00104 that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers).

In addition, any drug referred to herein may be in crystalline form either as free compound or as solvates (e.g. hydrates) and it is intended that both forms are within the scope of the present invention. Methods of solvation are generally known within the art.

PM00104 for use in accordance of the present invention may be prepared following the synthetic process disclosed in WO 01/87894, which is incorporated herein by reference.

Pharmaceutical compositions of PM00104 that can be used include solutions, suspensions, emulsions, lyophilised compositions, etc., with suitable excipients for intravenous administration. Preferably, PM00104 may be supplied and stored as a sterile lyophilized product, comprising PM00104 and excipients in a formulation adequate for therapeutic use. In particular a formulation comprising sucrose and a phosphate salt buffered to an adequate pH is preferred. Further guidance on PM00104 formulations is given in WO 2007/052076 which is incorporated herein by reference in its entirety.

Administration of PM00104, or pharmaceutical compositions thereof, or of pharmaceutical compositions comprising the compound is preferably by intravenous infusion. Infusion times of up to 72 hours can be used, more preferably between 1 and 24 hours, with either about 1, about 3 or about 24 hours most preferred. Short infusion times which allow treatment to be carried out without an overnight stay in hospital are especially desirable. However, infusion may be around 24 hours or even longer if required.

Preferably, the administration PM00104 is performed in cycles. In a preferred administration method an intravenous infusion of PM00104 is given to the patients typically the first day of each cycle and then the patients are allowed to recover for the remainder of the cycle. The preferred duration of each cycle is typically of 3 or 4 weeks; multiple cycles can be given as needed. Dose delays and/or dose reductions and schedule adjustments are performed as needed depending on individual patient condition and tolerance to treatments. For further guidance on PM00104 administration and dosages, see for example WO 2008/135792 which is incorporated herein by specific reference. Additional guidance on PM00104 administration and dosages can be found in Journal of Clinical Oncology, 2007 ASCO Annual Meeting Proceedings Part I. Vol 25, No. 18S (June 20 Supplement), 2007: 2517 and Eur. J. Cancer, 2008, Vol 6 (supl 12), page 57 Abstract No. 179, which are also incorporated herein by specific reference.

Although guidance for the dosage is given above, the correct dosage of the compound may change according to the particular formulation, the mode of application, and the particular situs, patient and tumor being treated. Other factors like age, body weight, sex, diet, time of administration, rate of excretion, condition of the patient, drug combinations, reaction sensitivities and severity of the disease shall be taken into account. Dose delays and/or dose reductions and schedule adjustments are performed as needed depending on individual patient condition and tolerance of treatments.

Depending on the type of tumor and the development stage of the disease, anticancer effects of the methods of treatment of the present invention include, but are not limited to, inhibition of tumor growth, tumor growth delay, regression of tumor, shrinkage of tumor, increased time to regrowth of tumor on cessation of treatment, slowing of disease progression, and prevention of metastasis. It is expected that when a method of treatment of the present invention is administered to a patient in need of such treatment, said method of treatment will produce an effect, as measured by, for example, the extent of the anticancer effect, the response rate, the time to disease progression, or the survival rate. In particular, the methods of treatment of the invention are suited for human patients, especially those who are relapsing or refractory to previous chemotherapy. First line therapy is also envisaged.

In one aspect, the invention provides a method for treating any mammal, notably a human, affected by MM, comprising administering to the affected individual a therapeutically effective amount of PM00104, or a pharmaceutically acceptable salt thereof.

In another aspect, the present invention is directed to a medical kit for administering PM00104, comprising printed instructions for administering PM00104 in the treatment of MM, and a pharmaceutical composition comprising PM00104, or a pharmaceutical acceptable salt thereof, and a pharmaceutically acceptable carrier or excipient.

In another aspect, the present invention also provides for a pharmaceutical composition comprising PM00104, or a pharmaceutically acceptable salt thereof, and a pharmaceutically acceptable carrier or excipient, to be used in the treatment of MM.

In another aspect, the invention further provides for the use of PM00104, or a pharmaceutically acceptable salt thereof, in the manufacture of a medicament for the treatment of MM.

In a further aspect, the invention provides PM00104, or a pharmaceutically acceptable salt thereof, for use in the treatment of MM.

PM00104, or a pharmaceutically acceptable salt thereof, may be used with other drugs to provide a combination therapy in the treatment of MM. The other drug may form part of the same composition, or be provided as a separate composition for administration at the same time or at different time. Preferably, the other drug is an antimyeloma agent including, but not limited to, dexamethasone, melphalan, doxorubicin, bortezomib, lenalidomide, prednisone, carmustine, etoposide, cisplatin, vincristine, cyclophosphamide, and thalidomide. Particularly preferred is the combination of PM00104, or a pharmaceutically acceptable salt thereof, with dexamethasone, melphalan, doxorubicin, bortezomib, lenalidomide, prednisone, carmustine, etoposide, cisplatin, vincristine, cyclophosphamide, and thalidomide, and even more preferred is the combination with dexamethasone, melphalan, doxorubicin, bortezomib, and lenalidomide. Effective combination therapies based on the used of three drugs, PM00104 or a pharmaceutically acceptable salt thereof plus two additional drugs are also encompassed by the present invention. Particularly preferred is the triple combination with dexamethasone and a third drug selected from melphalan, doxorubicin and lenalidomide.

The term "combination" as used throughout the specification, is meant to encompass the administration to a patient suffering from MM of the referred therapeutic agents in the same or separate pharmaceutical formulations, and at the same time or at different times. If the therapeutic agents are administered at different times they should be administered sufficiently close in time to provide for the potentiating or synergistic response to occur.

The following examples further illustrate the invention. They should not be interpreted as a limitation of the scope of the invention.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. In addition, unless otherwise stated, where values are given as ranges, the upper and lower values are specifically contemplated as preferred values.

EXAMPLES OF THE INVENTION

Example 1

Antiproliferative/Cytotoxic Effect of PM00104 Against MM Cells

Antitumor activity of PM00104 in MM was evaluated by using a cell line panel comprising the following 9 MM cell lines: MM1S, MM1R, MM144, RPMI8226, RPMI-LR5, U266, U266-LR7, OPM-1, and OPM-2. These cell lines were grown in RPMI 1640 medium with L-glutamine supplemented with antibiotics (penicillin at 100 U/mL, streptomycin at 100 µg/mL) and 10% fetal bovine serum (FBS) at 37° C. in a humidified atmosphere in the presence of 5% $CO_2$-95% air.

Cell lines were treated with increasing concentrations of the PM00104 (0.1-50 nM) for 24, 48 and 72 hours, and viability was analyzed by using 3-(4,5-dimethylthiazol-2-yl)-2,5-diphenyltetrazolium bromide (MTT) colorimetric assay. Briefly, MM cell lines were seeded at a density of 50,000 cells/200 µg/mL medium per well in 48-well plates, and treated with a determined drug dose and time. Two hours before the end of the treatment, a MTT solution (5 mg/mL) in PBS) was added and the tetrazolium salt was reduced by metabolically active cells to coloured formazan crystals. After solubilization of these crystals by overnight incubation with 10% SDS-HCl solution, absorbance was measured at 570 nm with correction at 630 nm. Results are presented as the mean±SD of quadruplicates of an experiment that was repeated at least twice.

Figure 1A:
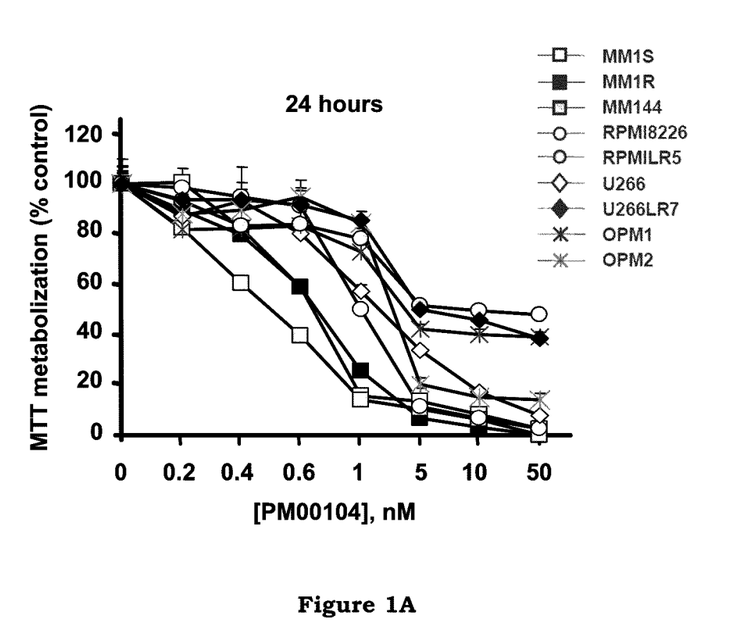
Figure 1B:
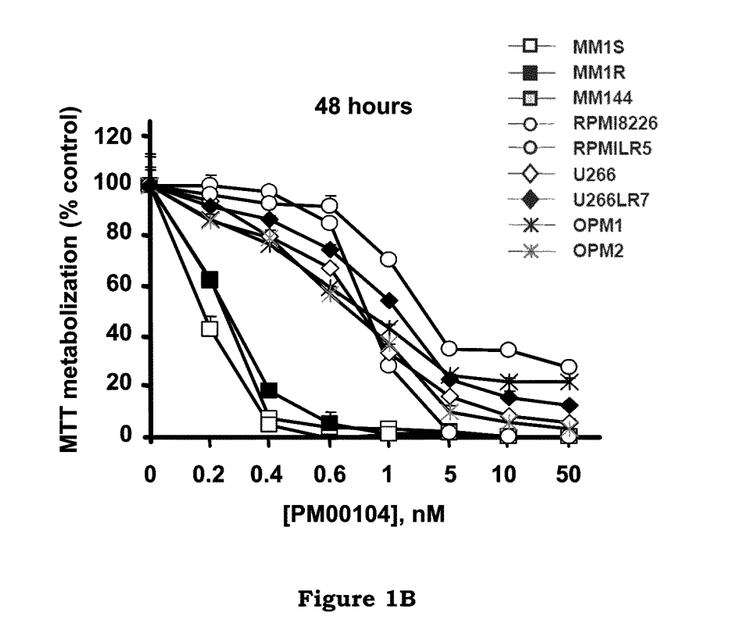
Figure 1C:
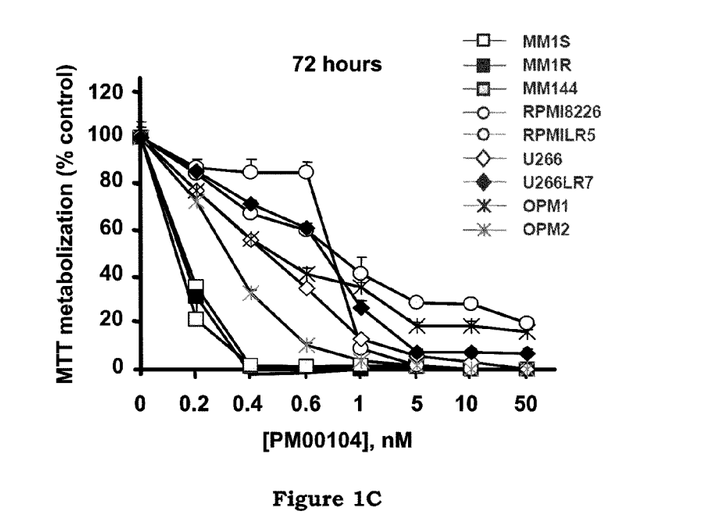

As shown in FIGS. 1A-C, all cell lines were very sensitive to the drug with $IC_{50}$'s at 48 hours ranging from picomolar concentrations in some cell lines (MM1S, MM1R and MM144) to low nanomolar (1-2 nM) in the less sensitive cell lines (RPMI8226, RPMI-LR5, U266, U266-LR7, OPM-1 and OPM-2). The sensitivity to PM00104 was independent of the pattern of resistance of the cell lines to conventional antimyeloma agents such as dexamethasone (all cell lines are resistant to dexamethasone with the exception of MM and MM 144) or melphalan (RPMI-LR5 and U266-LR7 are resistant to melphalan).

Additionally, the effect of PM00104 was further investigated ex vivo in cells isolated from bone marrow (BM) samples obtained from six patients with MM. Samples were lysed with ammonium chloride in order to remove red blood cells, and white cells were maintained in RPMI-1640 containing antibiotics (penicillin 100 U/ml, streptomycin 100 µg/ml) and 20% FBS. Subsequently, BM cells were incubated with different concentrations of PM00104 (1-50 nM) in six well plates for 18 hours at 37° C. To discriminate between myelomatous plasma cells (PC) and other BM cells, a multiparametric technique was performed in which cells were incubated for 15 minutes at room temperature in the dark with 5 µl Annexin-V-FITC (Bender MedSystems, Burlingame, Calif.) together with a combination of monoclonal antibodies against myeloma-associated antigens (anti-CD56-PE, anti-CD45-APC and anti-CD38-perCP/Cy5 (BD Biosciences)). A total of 50,000 cells were acquired on a FACScalibur flow cytometer (BD Biosciences) and analyzed with the "Paint-a-Gate" program. Apoptosis was analyzed based on the Annexin-V positivity in the different populations: tumour PCs as well as in normal residual lymphocytes and granulomonocytes. The percentage of Annexin V positive cells after treatment with PM00104 was calculated over the Annexin V negative cells (viable cells) in the control samples (without treatment).

Figure 2:
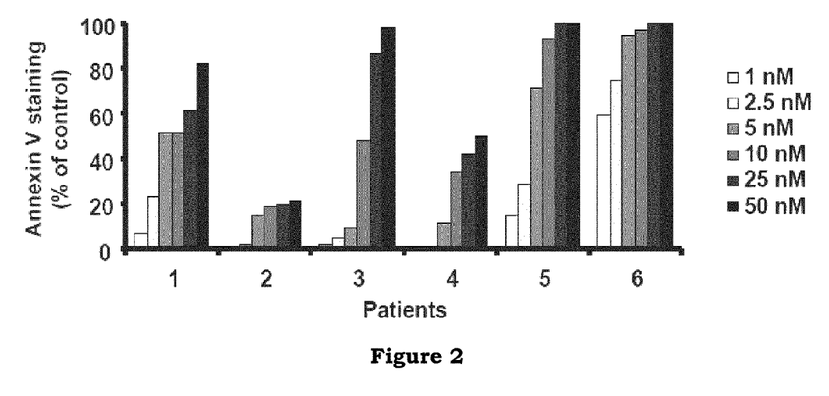
FIG. 2. Freshly isolated bone marrow cells obtained from six MM patients were treated ex vivo with PM00104 (1-50 nM) for 18 hours. After the incubation period, cells were stained with the combination of Annexin V-FITC, and three monoclonal antibodies against plasma cell surface antigens (CD38, CD56 and CD45) which allow the analysis of the induction of apoptosis in the myelomatous population. Results are given as the percentage of Annexin V positive cells related to the percentage of viable cells in the untreated sample.

Four out of the six samples analyzed were very sensitive to low concentrations of PM00104 including two samples obtained at diagnosis (patients 1 and 6), one at the moment of relapse (patient 3) and the remaining one was a plasma cell leukemia secondary to a relapsed MM (patient 5). Another sample corresponding to a secondary plasma cell leukemia (patient 4) had an intermediate sensitivity (FIG. 2).

Example 2

PM00104 Abrogates the Survival Advantage and Drug Resistance Induced by BM Microenvironment The presence of the BM microenvironment confers protection to MM through their adhesion or through the production of several cytokines such as IL-6 or IGF-I. In order to test whether PM00104 was able to inhibit this protective effect of the BM microenvironment, MM1S cells were incubated with IL-6 (1 nM) or IGF-I (10 nM), or co-cultured with BM stromal cells (BMSCs) for 48 hours, and then treated with increasing concentrations of PM00104. BMSCs were plated in 96-well culture dishes (50,000 cells/well) and allowed to reach confluence during 48 hours. Then, 30,000 myeloma cells were plated in RPMI 1640 containing 10% serum. Proliferation of MM cells was then assessed by Bromodeoxyuridine (BrdU) uptake (Maiso P et al. Br. J. Haematol. 2008, 141, 470-482). BrdU was added for the last 8 hours, and BrdU uptake was measured using a commercial kit (Roche Biochemicals), following the manufacturer's instructions.

Figure 3A:
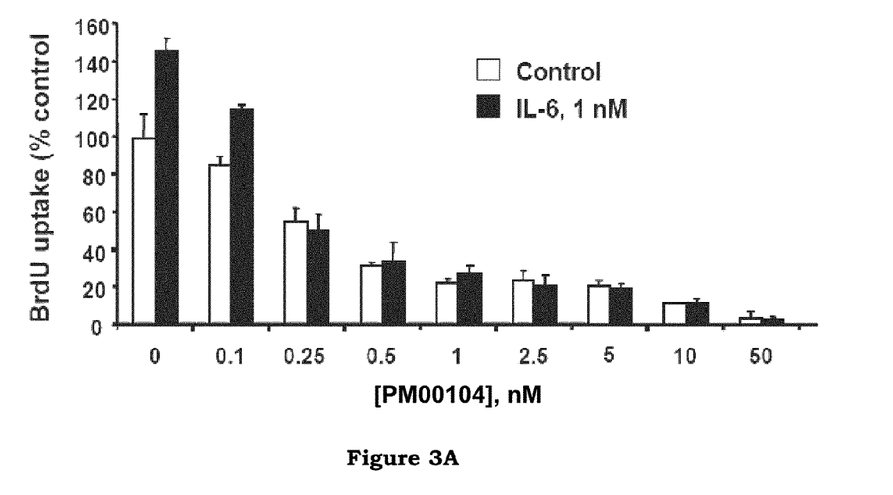
Figure 3B:
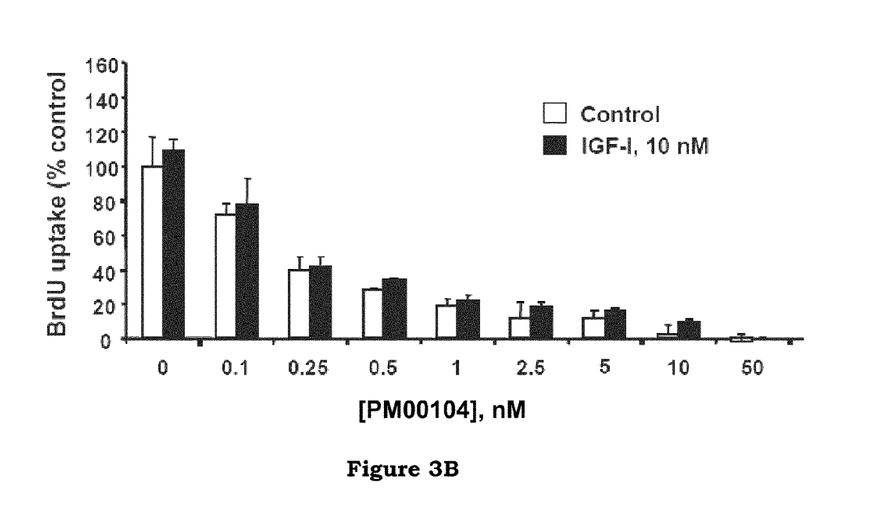
Figure 3C:
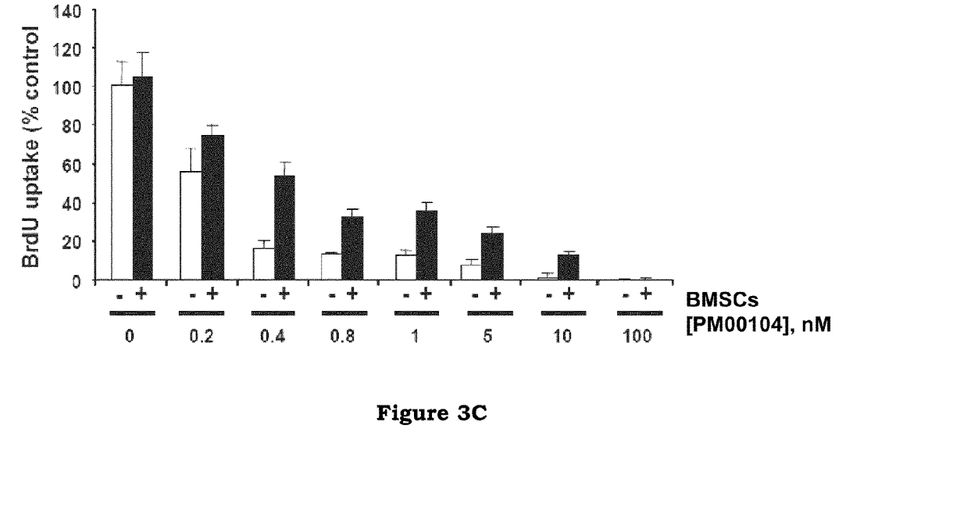
Figure 3D:
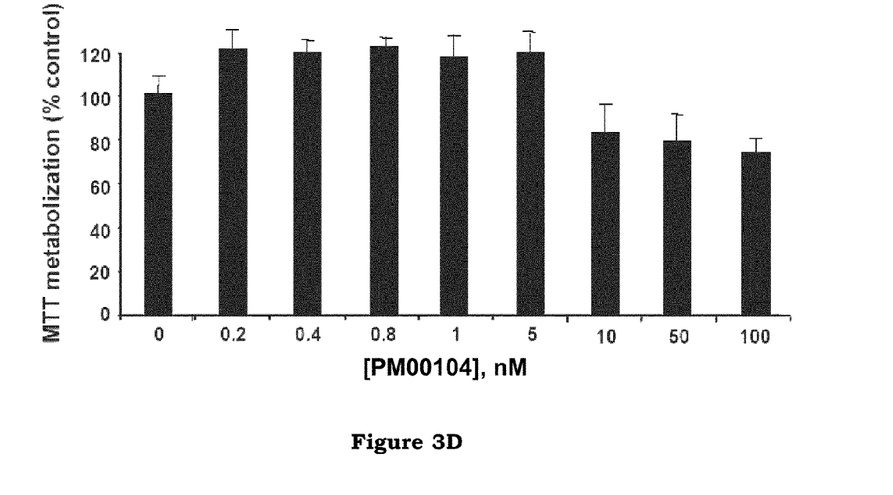

Despite the proliferative advantage to MM cells conferred by all these models, PM00104 completely abrogated the effect of the soluble cytokines IL-6 and IGF-I (FIGS. 3A and 3B), and largely inhibited the protective effect due to adhesion of plasma cells to BMSCs (FIG. 3C). In contrast, BMSCs were very resistant to the cytotoxic effect of PM00104 (FIG. 3D).

Example 3

In Vivo Anti-MM Efficacy of PM00104

The in vivo efficacy of PM00104 was studied in a model of human plasmocytoma xenografted in CB17-SCID mice. These experiments were performed using the very sensitive cell line MM1S and the less sensitive one OPM-1. Two cohorts of thirty mice were subcutaneously injected with each cell line and mice were randomized into three groups receiving vehicle alone, 0.8 mg/kg of PM00104, or 1 mg/Kg PM00104 intravenously (iv) once weekly for three doses.

CB17-SCID mice (The Jackson Laboratory, Bar Harbor, Me., USA) were subcutaneously inoculated into the right flank with $3\times10^6$ MM1S or OPM1 cells in 100 μL of RPMI-1640 medium and 100 μL of Matrigel (Becton Dickinson). When tumours became palpable, mice received PM00104 or vehicle alone. Treatment with PM00104 was given iv, at doses of 0.8 mg/kg and 1 mg/kg once weekly for three doses. The control group received the vehicle alone (sterile water for injection plus saline).

Caliper measurements of the tumour diameters were performed every day, and the tumour volume was estimated as the volume of an ellipse using the following formula: $V=4/3\pi\times(a/2)\times(b/2)^2$, where "a" and "b" correspond to the longest and shortest diameter, respectively. Animals were euthanized when their tumours reached 2 cm. Differences in tumour volumes between treated and control groups were evaluated using 1-way analysis of variance and Bonferroni post hoc tests. Survival was estimated from the day of initiation of treatment, and statistical differences were assessed by Kaplan-Meier curves with the Log Rank test. Statistical analyses were performed with the SPSS-15.0 software (SPSS Inc. Chicago, Ill., USA) and statistical significance was defined as $p<0.05$.

Figure 4A:
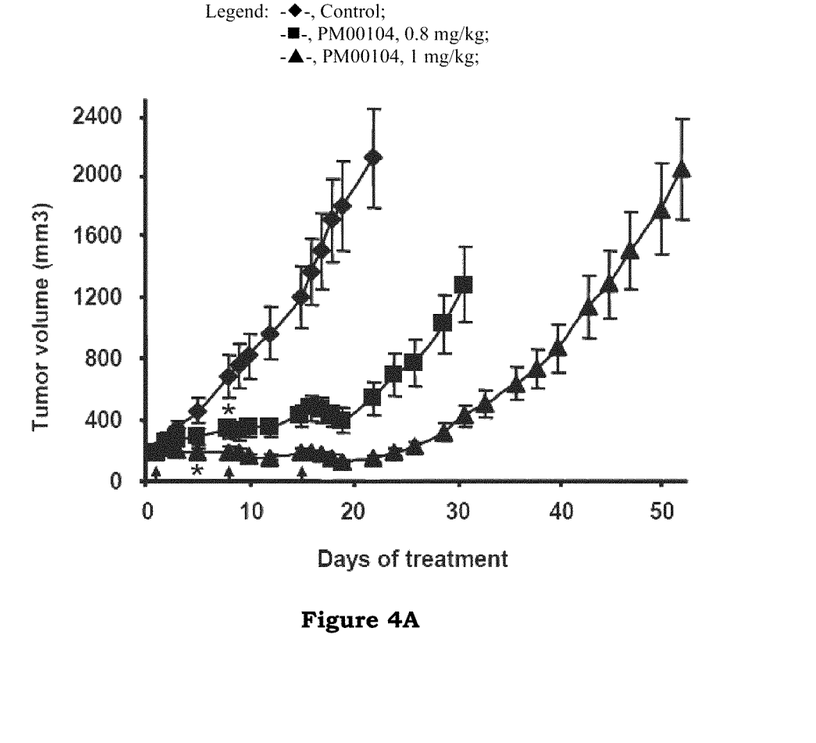
Figure 4B:
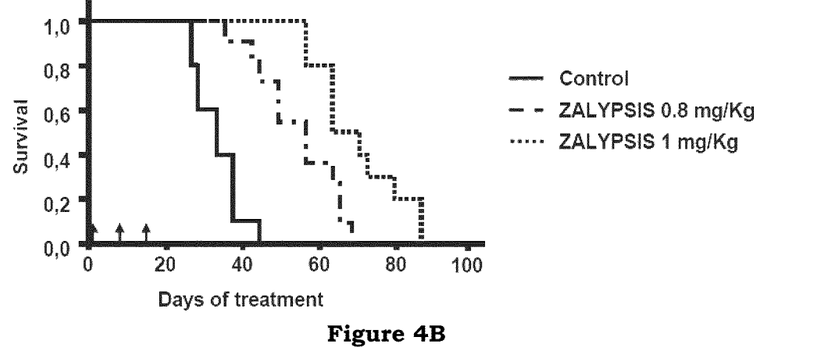
Figure 4C:
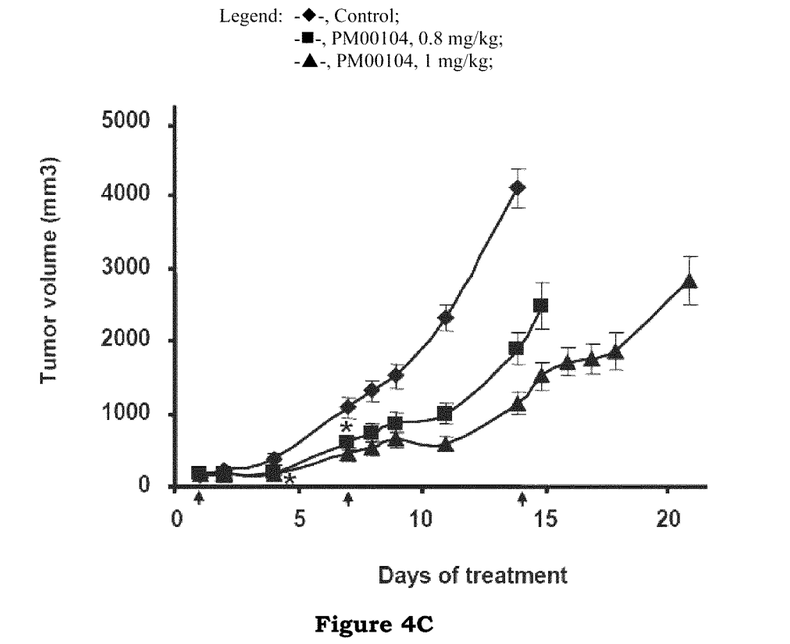
Figure 4D:
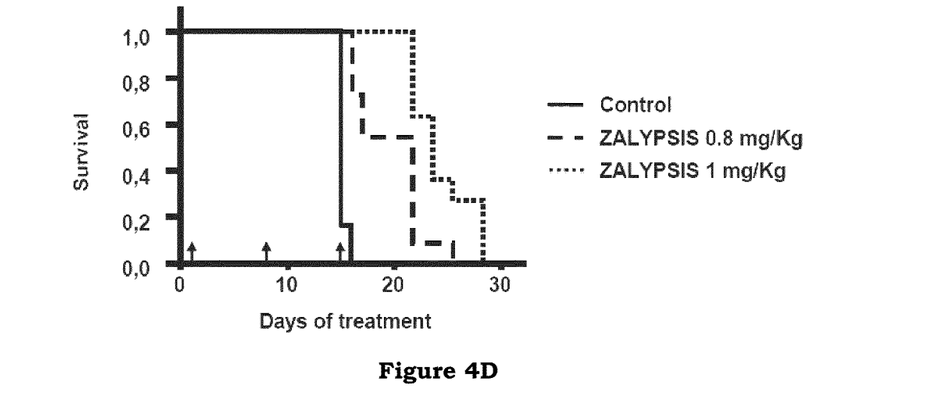

As shown in FIGS. 4A and 4C, both doses of PM00104 decreased the growth of the plasmocytomas with statistically significant differences. For the MM1S plasmocytomas, after 15 days of treatment, tumor volume was 1207±645, 420±242 and 176±78 mm³ (mean±SD) for the cohorts receiving vehicle, 0.8 mg/kg and 1 mg/kg, respectively ($p<0.001$ for the global comparison and for each of the treated vs control comparisons). In the less sensitive and more rapidly growing OPM-1 cell line, results were similar with tumor volumes after 14 days of treatment of 4091±903, 1879±731 and 1042±596 mm³ (mean±SD) for the same groups of mice ($p<0.001$ for all comparisons). This delay in tumor growth correlated with an increase in survival of treated mice as compared to the controls (FIGS. 4B and 4D). In this sense, in MM1S median±SE survivals were 29±3.9, 52±4.8 and 59±5.5 days for vehicle control, PM00104 0.8 mg/kg and PM00104 1 mg/kg, respectively (FIG. 4B); while survivals for the same groups in the OPM-1 plasmocytomas were: 14±0, 21±0.8 and 23±1.1 days (FIG. 4D). Differences were estimated with the Log Rank test that resulted in statistical significance differences as compared to the vehicle control for both doses in both xenografts ($p<0.001$).

Interestingly no significant systemic toxicity was associated with PM00104 treatment, and only a slight weight loss (around 10% of body weight as compared to the controls) was observed with the highest of PM00104 doses.

Example 4

PM00104 Potentiates the Efficacy of Conventional Anti-MM Agents

As treatment of most cancers, including MM, is based on combinations of drugs with different mechanisms of action, we studied the effect of PM00104 in combination with drugs normally used in the treatment of MM.

MM1S cells were treated for 72 hours, as described in example 1, with combinations of suboptimal doses of PM00104 and other antimyeloma agents such as dexamethasone, melphalan, doxorubicin, bortezomib and lenalidomide, in double and triple combinations. Cell viability was analyzed by MTT assay as described in example 1. The potency of the combination was quantified with the Calcusyn software (Biosoft, Ferguson, Mo.), which is based in the Chou Talalay method, that calculates a combination index (CI) with the following interpretation: CI>1: antagonistic effect, CI=1: additivity and CI<1 synergistic effect.

Figure 5A:
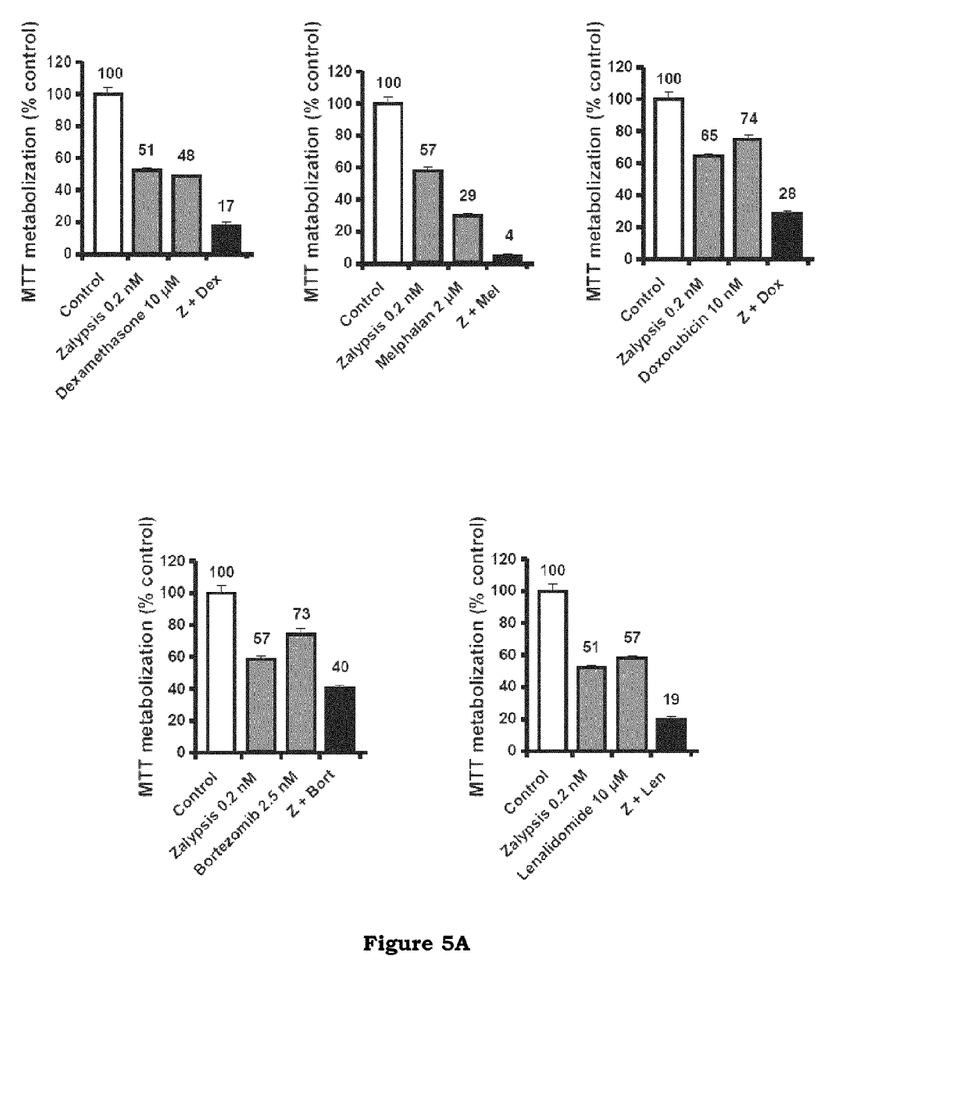

PM00104 clearly potentiated the effect of conventional antimyeloma agents such as dexamethasone, melphalan and doxorubicin in MM1S cells (FIG. 5A). PM00104 was also tested in combination with bortezomib and lenalidomide, two novel agents which have recently been included into the treatment armamentarium for MM patients with promising additive/synergistic results which were particularly evident in the combination with lenalidomide (FIG. 5A). Analyses of these data using the Chou and Talalay method indicated that PM00104 was synergistic with dexamethasone (CI=0.78), melphalan (CI=0.48), doxorubicin (CI=0.64) and lenalidomide (CI=0.55).

Figure 5B:
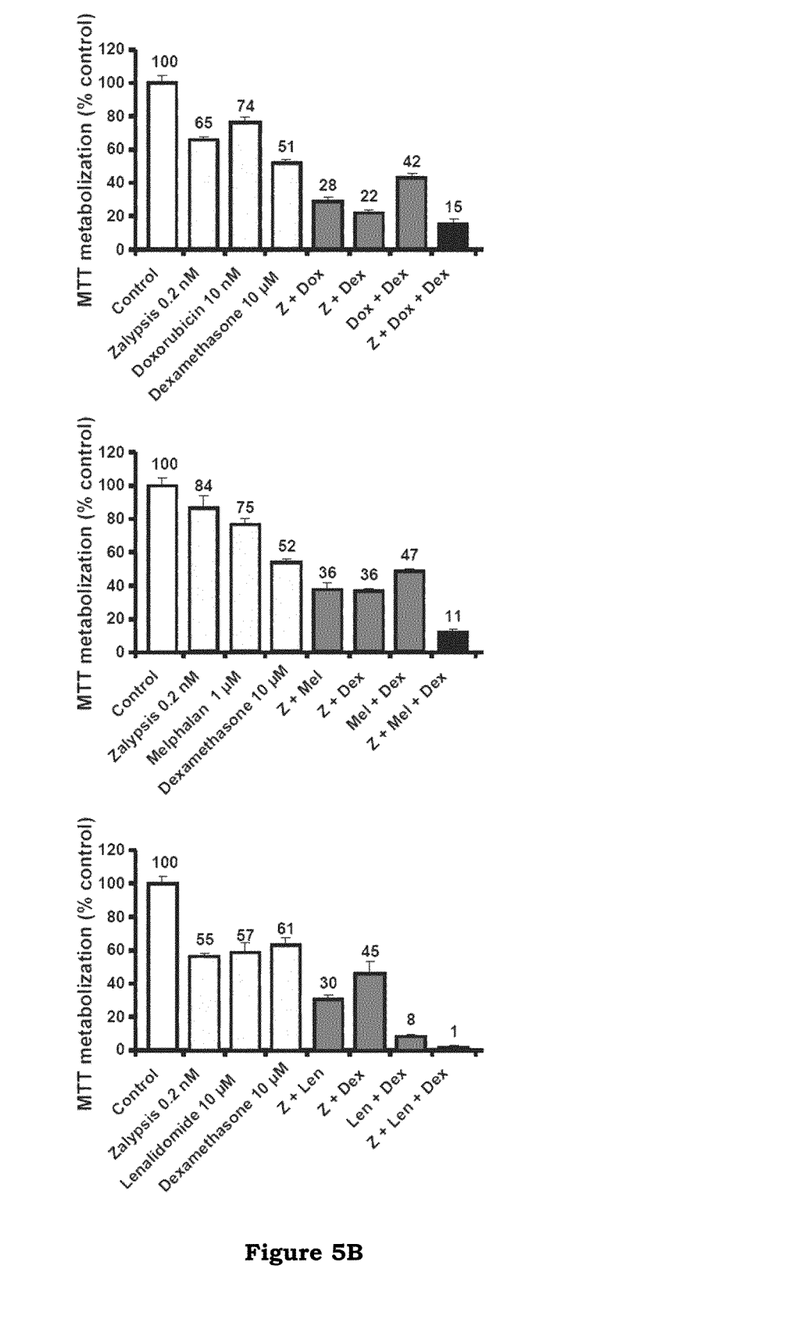

These promising results with double combinations prompted the investigation of triple combinations of the most synergistic compounds in the MM1S cell line. As can be observed in FIG. 5B, triple combinations of PM00104+dexamethasone+any of the following: melphalan, doxorubicin or lenalidomide, significantly improved the efficacy of the respective double combinations.

The invention claimed is:

1. A method for treating a mammal affected by multiple myeloma, comprising administering to the affected mammal a therapeutically effective amount of PM00104 or a pharmaceutical acceptable salt thereof.

2. The method according to claim 1, wherein the mammal is a human.

3. The method according to claim 1, wherein the mammal is relapsing or refractory to previous chemotherapy.

4. The method according to claim 1, wherein PM00104, or a pharmaceutically acceptable salt thereof, is used in combination with at least one other drug to provide a combination therapy.

5. The method according to claim 4, wherein the at least one other drug are antimyeloma agents.

6. The method according to claim 5, wherein the antimyeloma agent is selected from dexamethasone, melphalan, doxorubicin, bortezomib, lenalidomide, prednisone, carmustine, etoposide, cisplatin, vincristine, cyclophosphamide, and thalidomide.

7. The method according to claim 6, wherein the antimyeloma agent is selected from dexamethasone, melphalan, doxorubicin, bortezomib, and lenalidomide.

\* \* \* \* \*